(12) United States Patent
Frantzen

(10) Patent No.: US 6,299,635 B1
(45) Date of Patent: *Oct. 9, 2001

(54) RADIALLY EXPANDABLE NON-AXIALLY CONTRACTING SURGICAL STENT

(75) Inventor: John J. Frantzen, Laguana Niguel, CA (US)

(73) Assignee: Cook Incorporated, Bloomington, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/504,519

(22) Filed: Feb. 15, 2000

Related U.S. Application Data

(63) Continuation of application No. 08/939,703, filed on Sep. 29, 1997, now Pat. No. 6,042,606.

(51) Int. Cl.⁷ .................................................. A61F 2/06
(52) U.S. Cl. ............................................................ 623/1.17
(58) Field of Search .................................. 623/1.16, 1.15, 623/1.18, 1.17; 606/198

(56) References Cited

U.S. PATENT DOCUMENTS

| | | |
|---|---|---|
| D. 380,266 | 6/1997 | Boatman et al. . |
| D. 380,831 | 7/1997 | Kavteladze et al. . |
| 5,104,404 | 4/1992 | Wolff . |
| 5,133,732 | 7/1992 | Wiktor . |
| 5,139,480 | 8/1992 | Hickle et al. . |
| 5,195,984 | 3/1993 | Schatz . |
| 5,242,399 | 9/1993 | Lau et al. . |
| 5,314,444 | 5/1994 | Gianturco . |

(List continued on next page.)

FOREIGN PATENT DOCUMENTS

| | | |
|---|---|---|
| 0679372 | 4/1995 | (EP) . |
| 9828035 | 7/1998 | (WO) . |

* cited by examiner

Primary Examiner—Cary E. O'Connor
(74) Attorney, Agent, or Firm—Anton P. Ness

(57) ABSTRACT

A radially expandable and contractible surgical stent 10 is provided formed from a shape memory material such as a Nickel-Titanium alloy. The stent 10 includes a series of wave-like struts 20 spaced apart by gaps 60. Each gap 60 is spanned by tie bars 70 at a maximum 64 width portion of the gap 60 or by an angled link 80 or a straight link 90 at a minimum 62 width portion of a gap 60. Hence, axial expansion or contraction of the stent 10 is avoided when the stent 10 is radially expanded or contracted. Each strut 20 is formed from a series of substantially linear legs 30 joined together by free bends 40 or attachment bends 50. The legs 30 and bends 40, 50 can be provided with an enhanced thickness 36 to augment resistance of the stent 10 to fracture when radially expanded or contracted. The stent 10 can be radially contracted to a diameter less than one-fourth of its radially expanded configuration when in a martensite phase. The stent 10 returns to a shape memory austenite phase when the stent 10 is unloaded or loaded below its yield strength and has a temperature above its transition temperature. The stent 10 can thus be easily collapsed and implanted within a body lumen for later radial expansion to support the body lumen.

10 Claims, 6 Drawing Sheets

U.S. PATENT DOCUMENTS

| | | |
|---|---|---|
| 5,421,955 | 6/1995 | Lau et al. . |
| 5,425,739 | 6/1995 | Jessen . |
| 5,441,515 | 8/1995 | Khosravi et al. . |
| 5,443,477 | 8/1995 | Marin et al. . |
| 5,449,373 * | 9/1995 | Pinchaski et al. ............... 606/198 |
| 5,494,029 | 2/1996 | Lane et al. . |
| 5,496,277 | 3/1996 | Termin et al. . |
| 5,507,767 | 4/1996 | Maeda et al. . |
| 5,507,771 | 4/1996 | Gianturco . |
| 5,514,154 | 5/1996 | Lau et al. . |
| 5,522,882 | 6/1996 | Gaterud et al. . |
| 5,531,741 | 7/1996 | Barbacci . |
| 5,545,210 | 8/1996 | Hess et al. . |
| 5,549,662 | 8/1996 | Fordenbacher . |
| 5,562,641 | 10/1996 | Flomenblit et al. . |
| 5,569,295 | 10/1996 | Lam . |
| 5,591,195 | 1/1997 | Taheri et al. . |
| 5,591,197 | 1/1997 | Orth et al. . |
| 5,603,721 | 2/1997 | Lau et al. . |
| 5,632,760 | 5/1997 | Sheiban et al. . |
| 5,636,641 | 6/1997 | Fariabi . |
| 5,697,971 | 12/1997 | Fischell et al. . |
| 5,718,713 * | 2/1998 | Frantzen ............... 606/198 |
| 5,741,327 | 4/1998 | Frantzen . |
| 5,746,691 | 5/1998 | Frantzen . |
| 5,755,781 * | 5/1998 | Jayaraman ............... 623/1 |
| 5,807,404 * | 9/1998 | Richter ............... 623/1 |
| 5,843,175 | 12/1998 | Frantzen . |
| 5,853,419 | 12/1998 | Imran . |
| 5,868,782 | 2/1999 | Frantzen . |

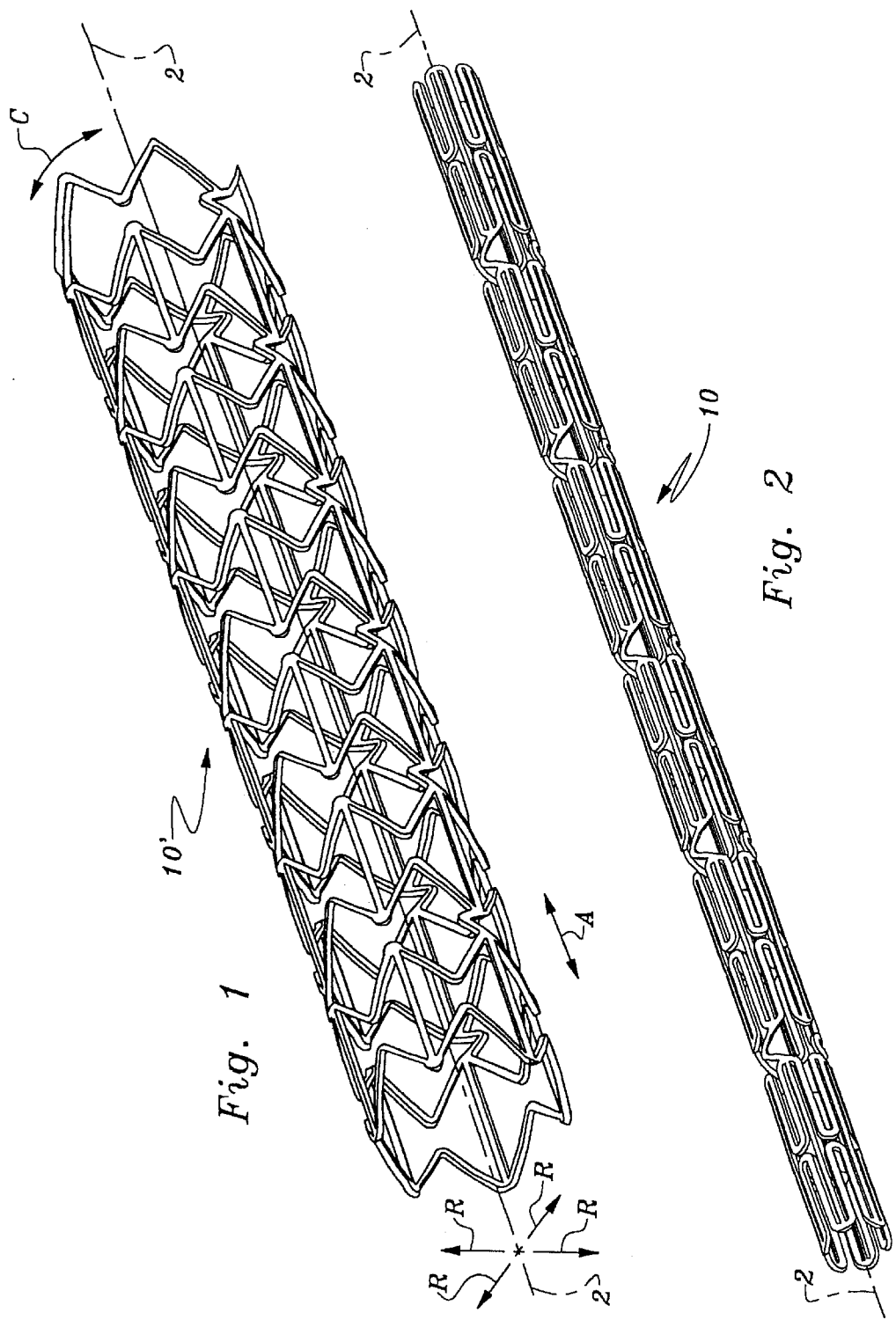

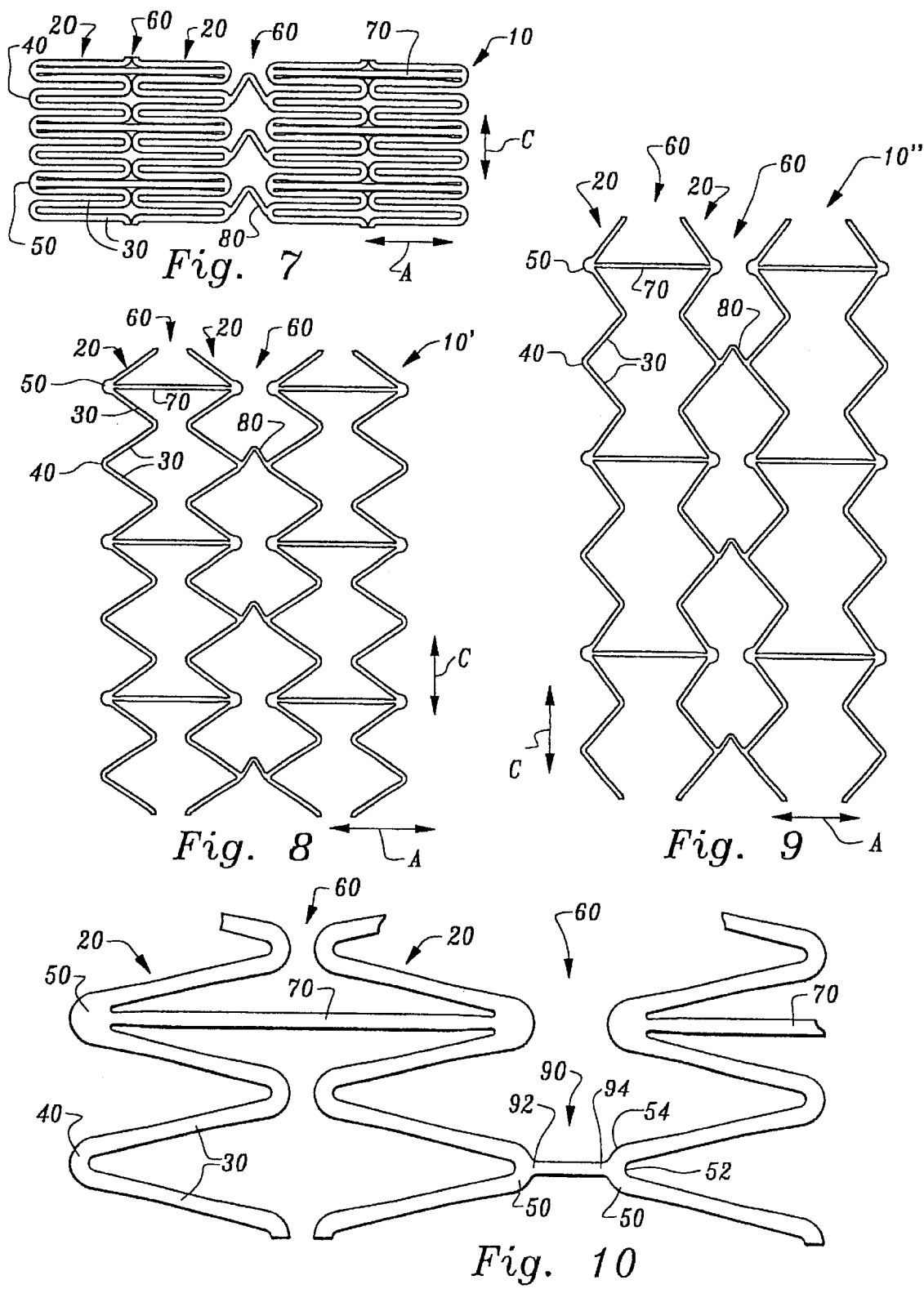

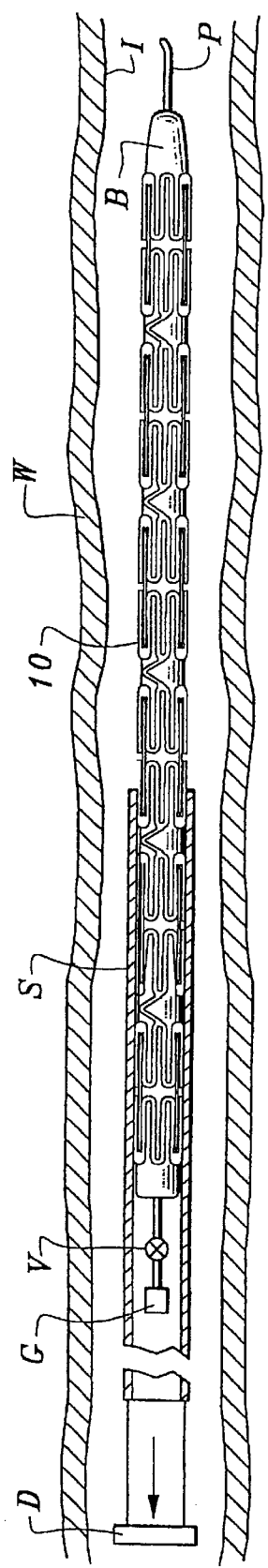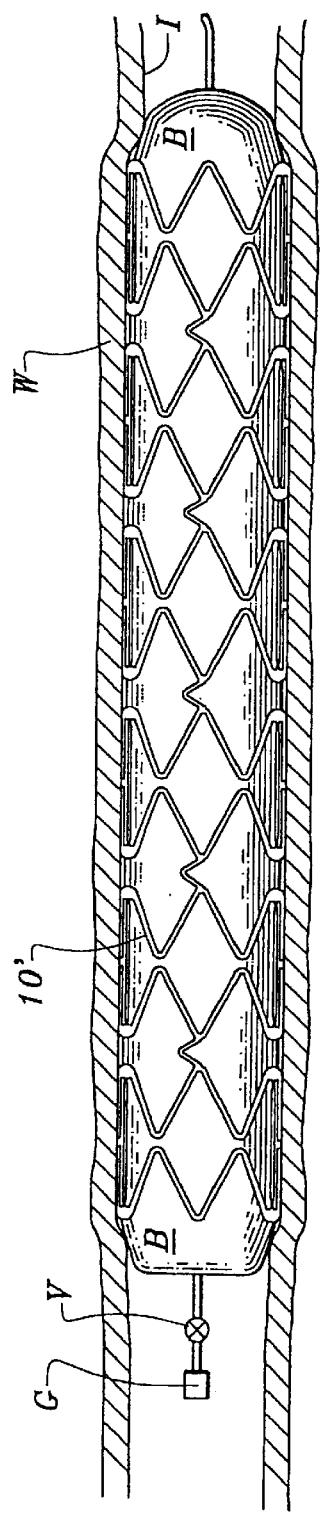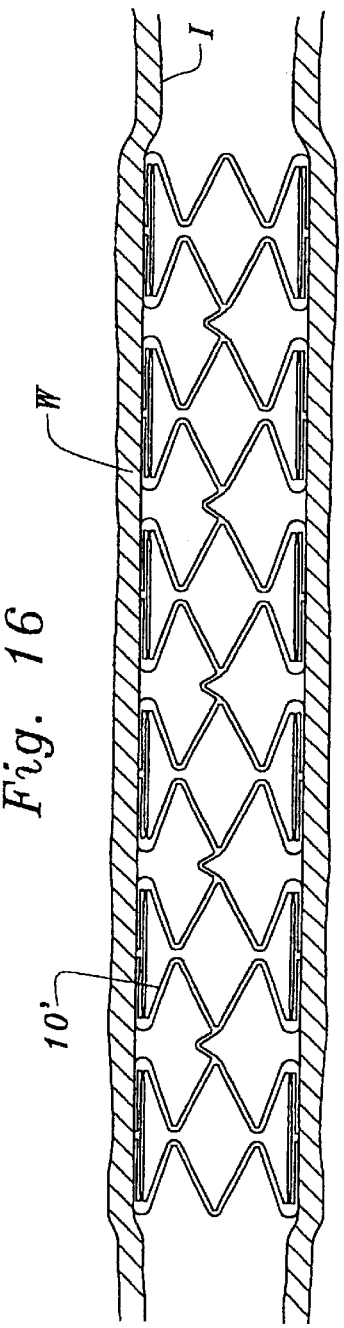

RADIALLY EXPANDABLE NON-AXIALLY CONTRACTING SURGICAL STENT

CROSS-REFERENCE TO RELATED APPLICATION

This is a Continuation application of U.S. patent application Ser. No. 08/939,703 filed Sep. 29, 1997, now U.S. Pat. No. 6,042,606.

FIELD OF THE INVENTION

The following invention relates to surgical stents of a generally cylindrical configuration which can be surgically implanted into a body lumen, such as an artery, and radially expanded. More specifically, this invention relates to radially expandable surgical stents having a high radial strength for implantation in body lumens which experience radial loads.

BACKGROUND OF THE INVENTION

Surgical stents have long been known which can be surgically implanted into a body lumen, such as an artery, to reinforce, support, repair or otherwise enhance the performance of the lumen. For instance, in cardiovascular surgery it is often desirable to place a stent in the coronary artery at a location where the artery is damaged or is susceptible to collapse. The stent, once in place, reinforces that portion of the artery allowing normal blood flow to occur through the artery. One form of stent which is particularly desirable for implantation in arteries and other body lumens is a cylindrical stent which can be radially expanded from a first smaller diameter to a second larger diameter. Such radially expandable stents can be inserted into the artery by being located on a catheter and fed internally through the arterial pathways of the patient until the unexpanded stent is located where desired. The catheter is fitted with a balloon or other expansion mechanism which exerts a radial pressure outward on the stent causing the stent to expand radially to a larger diameter. Such expandable stents exhibit sufficient rigidity after being expanded that they will remain expanded after the catheter has been removed.

Radially expandable stents come in a variety of different configurations to provide optimal performance to various different particular circumstances. For instance, the patents to Lau (U.S. Pat. Nos. 5,514,154, 5,421,955, and 5,242,399), Baracci (U.S. Pat. No. 5,531,741), Gaterud (U.S. Pat. No. 5,522,882), Gianturco (U.S. Pat. Nos. 5,507,771 and 5,314,444), Termin (U.S. Pat. No. 5,496,277), Lane (U.S. Pat. No. 5,494,029), Maeda (U.S. Pat. No. 5,507,767), Marin (U.S. Pat. No. 5,443,477), Khosravi (U.S. Pat. No. 5,441,515), Jessen (U.S. Pat. No. 5,425,739), Hickle (U.S. Pat. No. 5,139,480), Schatz (U.S. Pat. No. 5,195,984), Fordenbacher (U.S. Pat. No. 5,549,662) and Wiktor (U.S. Pat. No. 5,133,732), each include some form of radially expandable stent for implantation into a body lumen.

Each of these prior art stents suffer from a variety of drawbacks which make them less than ideal. For instance, many of these stents are formed from stainless steel or other materials which have a relatively low yield strength. Hence, if the body lumen is subjected to radial loads and related radial stresses, the stents are susceptible to collapse or other permanent deformation in an undesirable manner. If such stents are provided with segments of greater thickness to enhance their strength, they become too thick to be effectively collapsed for insertion and later expansion within the body lumen.

One material for forming higher strength radially expandable surgical stents is a shape memory Nickel-Titanium alloy. Shape memory Nickel-Titanium alloys and other shape memory alloys are unique in that they have two distinct solid phases. A high yield strength austenite phase (195–690 MPa) and a lower yield strength martensite phase (70–140 MPa). The material can be selectively transformed between the austenite phase and the martensite phase by altering a temperature of the shape memory Nickel-Titanium alloy. For instance, it is known to form the Nickel-Titanium alloy so that the stent is in the martensite phase when chilled to a temperature below body temperature and to be in the austenite phase when the stent is at body temperature.

Additionally, when such shape memory alloys are stressed beyond their yield strength while in the martensite phase, not to exceed certain maximum amounts of strain, the alloy has a "memory" of its shape before its yield strength in the martensite phase was exceeded so that when the alloy is heated and transformed into its austenite phase it returns to the shape it exhibited before it was plastically deformed in the martensite phase. In radially expandable surgical stents, this shape memory has been used to collapse the stent to a small diameter when in its martensite phase and then heat the stent up to body temperature and transform the stent into its austenite phase where it radially expands back to its original expanded diameter and exhibits a desired strength and size for supporting walls of the body lumen in which it is implanted. Hence, the relatively high yield strength of the shape memory alloy stent in its austenite phase provides beneficial characteristics for supporting the body lumen while the martensite phase for the shape memory alloy stent is utilized to allow the stent to be easily radially contracted and deformed during implantation of the stent.

While such shape memory Nickel-Titanium alloy stents are generally effective, known shape memory Nickel-Titanium stents have exhibited certain deficiencies. For instance, when such prior art shape memory Nickel-Titanium stents are radially expanded they tend to contract axially, enhancing the difficulty experienced by a surgeon in precisely implanting the stent where desired. Additionally, the limited degree of collapsibility of known prior art shape memory Nickel-Titanium stents has enhanced the difficulty of their implantation in many body lumens. Accordingly, a need exists for shape memory Nickel-Titanium alloy stents which have a configuration which beneficially overcomes the drawbacks of known prior art shape memory Nickel-Titanium alloy stents.

SUMMARY OF THE INVENTION

This invention provides a radially expandable stent formed of shape memory Nickel-Titanium alloy which exhibits little or no contraction along an entire axial length thereof when the stent is expanded radially. The stent includes a series of struts which act as circumferential segments circumscribing the cylindrical contour of the stent. Each strut is aligned with a separate plane perpendicular to a central axis of the cylindrical contour of the stent and parallel to other planes to which adjacent struts are aligned. The stent can have various different numbers of struts joined together to form the stent. However, at least two end struts are provided including a front end strut and a rear end strut which define ends of the cylindrical contour of the stent. Intermediate struts are also typically provided between the two end struts.

Each of these struts exhibits a wave-like shape as they circumscribe the cylindrical contour of the stent. Thus, each strut has a series of bends which have troughs and crests alternating along the length of each strut. Substantially linear legs extend between each bend. Each trough defines a portion of the strut which is most distant from adjacent struts and each crest defines a portion of the strut closest to adjacent struts. An amplitude of each strut, defined by the distance between the bottom of each trough and the top of each crest is modified when the stent is radially expanded so that the amplitude is decreased.

The end struts are attached to adjacent intermediate struts by tie bars which act as axial segments connecting the two adjacent struts together. Tie bars can also connect adjacent intermediate struts to each other. Each tie bar attaches to the struts adjacent thereto through a first end of the tie bar and a second end of the tie bar. Both the first end and the second end are located within troughs of the struts. Thus, the tie bars span a gap between adjacent struts at a maximum width portion of the gap. Not all of the gaps are necessarily spanned by tie bar axial elements. Rather, separate intermediate circumferential segments can be attached to each other through links which connect to the intermediate segments at locations spaced away from the troughs thereof.

To further enhance the collapsibility and expandability of the stent as well as an overall strength of the stent, the legs of the struts preferably do not have a constant thickness. Rather, ends of each leg adjacent bends in the struts preferably have a greater thickness than a middle of each leg between the ends of each leg. Also, the bends in the struts preferably have a greater width between an inner radius on a trough side of each bend and an outer radius on a crest side of each bend. This enhanced width of the bends and enhanced thickness of the legs near the ends provides maximum strength for the struts at locations on the struts where stresses are concentrated and fracture of the struts is most likely. Hence, greater resistance to fracture of the struts of the stent is provided.

Because the legs are preferably substantially linear, the stent can be radially contracted until the adjacent legs of each strut are substantially parallel to each other, potentially to the point where adjacent legs abut each other.

To form the shape memory Nickel-Titanium alloy stent the following basic procedure can be followed. Initially, a cylindrical tube of the desired Nickel-Titanium alloy is provided having a diameter intermediate between a desired expanded configuration and a desired collapsed configuration. This cylindrical tube is cut until only the series of circumferential segments and axial segments remain defining the generally cylindrical contour of the stent. The stent is then forced onto a mandrel having a diameter matching a desired radially expanded diameter until the stent has been expanded to the desired radially expanded diameter. The stent is then heat treated at a temperature of at least 350° C. until the shape memory of the stent in its austenite phase has a diameter matching that of the mandrel and the transformation temperature is set as desired. For instance, a transformation temperature of about 10° C. allows the stent to be fully in its austenite phase at body temperatures. The stent can then be removed from the mandrel.

The stent can be cooled until it transforms into its martensite phase. While in the martensite phase, the stent is radially collapsed down to its desired collapsed diameter configuration. When the stent is ready for implantation within a body lumen, the stent in its collapsed configuration is inserted with a catheter to the desired implantation site. The body temperature of the patient causes the stent to transform into its austenite phase and the shape memory of the Nickel-Titanium alloy causes the stent to expand radially to the desired radially expanded configuration. To ensure proper radial expansion of the stent from its collapsed configuration to its expanded configuration, a sleeve can be placed over an outer surface of the stent until the stent is in the desired position and a balloon can be located within an interior of the stent which can be radially expanded to assist the stent in fully expanding to its radially expanded shape memory configuration. The relatively high yield strength elastic austenite phase Nickel-Titanium stent is then in place within the body lumen to support the body lumen while resisting deformation when receiving radial loads.

OBJECTS OF THE INVENTION

Accordingly, a primary object of the present invention is to provide a radially expandable and contractible Nickel-Titanium shape memory stent which does not contract axially when expanded radially.

Another object of the present invention is to provide a surgical stent which exhibits little or no axial contraction at ends thereof when expanded radially.

Another object of the present invention is to provide a stent which exhibits sufficient flexibility to allow a central axis thereof to bend, especially when the stent is being threaded through arterial pathways within a patient.

Another object of the present invention is to provide a Nickel-Titanium surgical stent which is formed from a series of struts which form circumferential segments circumscribing a cylindrical contour of the stent, the individual struts joined together by tie bars which act as axial segments restraining the struts from contracting together when expanded radially.

Another object of the present invention is to provide a surgical stent which has a configuration which lends itself to manufacture from a variety of techniques including machining, photo-etching, laser cutting and other precision low cost techniques.

Another object of the present invention is to provide a surgical stent which has a configuration which exhibits the strength necessary to support a body lumen when implanted therein and radially expanded.

Another object of the present invention is to provide a surgical stent which can be located within a body lumen by a surgeon with a high degree of locational precision.

Another object of the present invention is to provide a Nickel-Titanium surgical stent which can be radially expanded to over four times its radially contracted diameter, does not substantially contract axially when radially expanded and which has sufficient flexibility to match a flexibility of a guide wire of a stent positioning catheter utilized to position the stent.

Another object of the present invention is to provide a shape memory surgical stent which can be radially contracted when in a martensite phase for ease in implantation within a body lumen and later radially expanded to a "memorized" shape when the stent transitions into an austenite phase.

Another object of the present invention is to provide a surgical stent which exhibits a high yield strength (i.e. at least 195 MPa and up to 690 MPa) such that the stent resists plastic deformation when radial collapsing loads are encountered, such as impacts to the patient adjacent the body lumen where the stent is implanted.

Another object of the present invention is to provide a surgical stent which can be implanted in body lumens on extremities of a patient without substantial risk of collapse or other damage to the stent when blows are experienced by the patient adjacent the site of surgical implantation of the stent.

Another object of the present invention is to provide a Nickel-Titanium surgical stent which has a configuration which allows the stent to be radially expanded from a radially collapsed configuration to a radially expanded configuration up to four or more times the size of its collapsed configuration without segments of the stent experiencing fractures.

Other further objects of the present invention will become apparent from a careful reading of the included description and claims and from a review of the drawing figures.

BRIEF DESCRIPTION OF THE DRAWINGS

FIG. 1 is a perspective view of a Nickel-Titanium stent of a basic configuration in a radially expanded configuration.

FIG. 2 is a perspective view of the basic stent of FIG. 1 in a radially collapsed configuration.

FIG. 7 is a cylindrical projection of a portion of a radially collapsed stent similar to that which is shown in FIG. 1 but without width enhancement adjacent bends in the struts.

FIG. 8 is a cylindrical projection of a portion of that which is shown in FIG. 3 with said stent partially radially expanded.

FIG. 9 is a cylindrical projection of that which is shown in FIG. 8 after full radial expansion of the stent.

FIG. 10 is a detail of a portion of that which is shown in FIG. 3 except that certain axial segments are configured as straight links.

FIG. 15 is a sectional view of a body lumen with the stent of FIGS. 1–5 in the process of being implanted with the implantation apparatus of FIG. 14.

FIG. 16 is a sectional view similar to that which is shown in FIG. 15 revealing an intermediate step in the implantation of the stent of FIGS. 1–5.

FIG. 17 is a sectional view of a body lumen after the stent of FIGS. 1–5 has been successfully implanted and radially expanded within the body lumen.

DESCRIPTION OF THE PREFERRED EMBODIMENT

Figure 3:
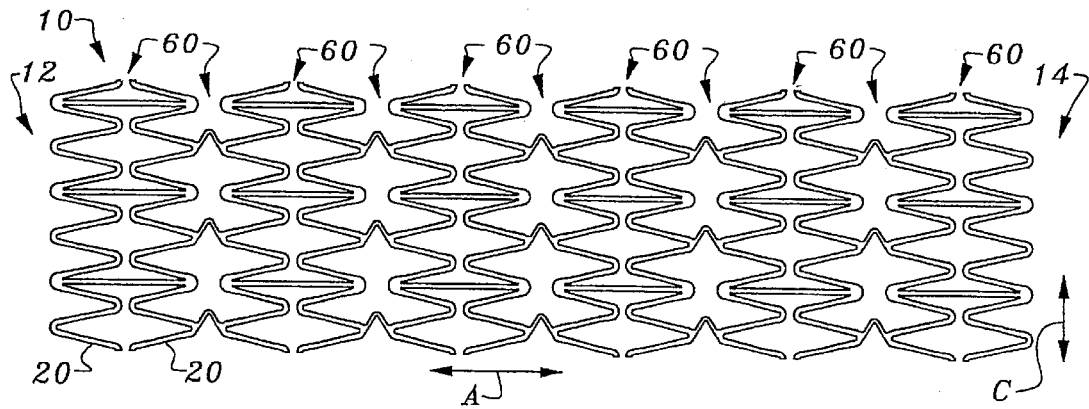
FIG. 3 is a cylindrical projection of the basic stent of FIGS. 1 and 2.
Figure 4:
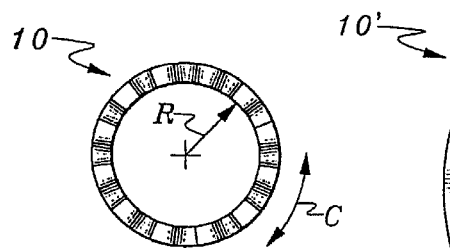
FIG. 4 is an end view of that which is shown in FIG. 1.
Figure 5:
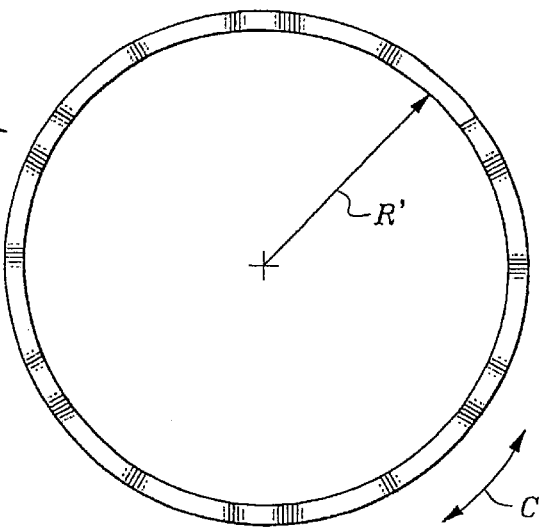
FIG. 5 is an end view of that which is shown in FIG. 2.

Referring to the drawings wherein like reference numerals represent like parts throughout, reference numeral 10 is directed to a radially expandable and contractible surgical stent formed from a shape memory material such as a Nickel-Titanium alloy. The stent 10 is cylindrical in contour with a series of struts 20 (FIG. 3) forming circumferential segments of the stent 10 which exhibit a wave-like contour. The struts 20 can hence be collapsed to reduce a radius of the stent 10 and expanded to increase a radius of the stent 10 (along Arrow R of FIG. 1). An axial length, along arrow A, remains constant when the stent 10 is radially collapsed and expanded along arrow R.

In essence, and with particular reference to FIGS. 1–6, the stent 10 has the following basic configuration. A series of struts 20 having a wave-like contour with a series of troughs and crests extend circumferentially, along arrow C, at a location of substantially constant radial distance away from a central axis 2. Gaps 60 are located between each pair of adjacent struts 20. The struts 20 provide circumferential segments for the stent 10. Axially extending segments in the form of tie bars 70 and angled links 80 span the gaps 60 and join adjacent struts 20 together. The tie bars 70 attach to adjacent struts 20 at attachment bends 50 in the struts 20 and on a trough side 52 of the attachment bends 50. The angled links 80, or optionally the straight links 90 (FIG. 10) attach to adjacent struts 20 at attachment bends 50 on a crest side 54 of the attachment bends 50. In this way, radial expansion, along arrow R, does not cause contraction of an axial length, along arrow A, of the stent 10. Each gap 60 is either spanned only by tie bars 70 or spanned only by angled links 80 or straight links 90. Preferably, the gaps 60 with tie bars 70 alternative with the gaps 60 spanned by the angled links 80 or straight links 90.

The wave-like contour of each strut 20 preferably is formed from a series of substantially straight legs 30 extending between free bends 40 and attachment bends 50. The free bends 40 do not have any tie bars 70, angled links 80 or straight links 90 coupled thereto. The attachment bends 50 have either a tie bar 70, angled link 80 or straight link 90 attached thereto. A thickness 36 of the legs 30 can be enhanced adjacent ends 32 of the legs 30 and a width 46 of the free bends 40 and a width 56 of the attachment bends 50 can be enhanced with respect to a thickness of the middle 34 of the legs 30, such that regions of potential fracture of the struts 20 are strengthened.

Because the stent 10 is formed from a shape memory Nickel-Titanium material the stent 10' has a radially expanded configuration (FIG. 1) when the stent 10' is in a position corresponding to its shape memory and when the stent 10' is in an austenite phase. The stent 10 can be cooled below a transition temperature to undergo a phase change into a martensite phase and then be radially collapsed to its radially collapsed configuration (FIG. 2) without losing its shape memory. Hence, when the stent 10' is heated above its transition temperature and converted back into its austenite phase it tends to return back to its radially expanded configuration (FIG. 1) and exhibits a higher yield strength corresponding to its austenite phase.

Figure 6:
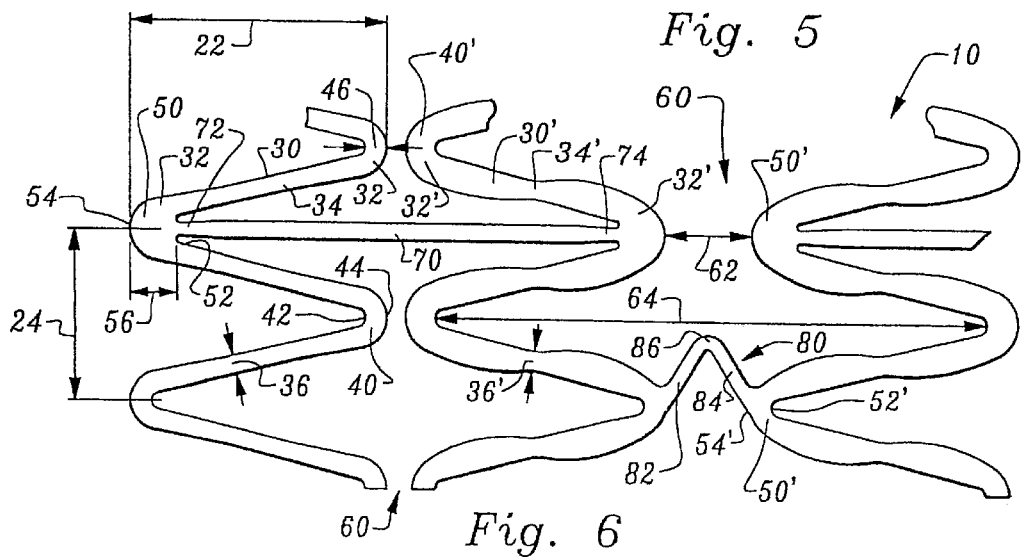
FIG. 6 is a detail of a portion of that which is shown in FIG. 3 with some of the struts shown therein featuring legs with variable thicknesses to enhance a strength of the struts.

More specifically, and with particular reference to FIGS. 3 and 6, details of the configuration of the struts 20 of the stent 10 are provided. Each strut 20 is preferably similar in size and shape to all of the other struts 20 of the stent 10. The struts 20 are integrally formed with other portions of the stent 10 from a shape memory material, such as a Nickel-Titanium alloy, having the desired characteristics for surgical implantation into a body lumen. Specifically, known Nickel-Titanium alloys have an austenite phase with a high yield strength (195–690 MPa) and a martensite phase with a lower yield strength (70–140 MPa) with the material having a shape memory which causes the stent to return to its memorized austenite phase shape when the temperature of the stent is above a transition temperature between the martensite phase and the austenite phase. The transition temperature is selected to be below typical body temperature so that the stent 10 can be easily contracted when cooled below the transition temperature but will be in its austenite phase once implanted and at body temperature.

Each strut 20 extends as a circumferential segment, along arrow C (FIGS. 1 and 3-5), and has a wave-like pattern as the strut 20 circumscribes the cylindrical contour of the stent 10. The wave-like contour of the stent 20 is preferably uniform such that the strut 20 has a uniform amplitude 22 (FIG. 6) and a uniform wavelength 24. This amplitude 22 and wavelength 24 are altered when a diameter of the stent 10 is modified.

Each strut 20 is preferably formed from a series of substantially linear legs 30. While the legs 30 are substantially linear, they may in fact curve slightly to match the cylindrical contour of the stent 10. The legs 30 have ends 32 where each leg 30 is attached to adjacent free bends 40 or attachment bends 50. Each leg 30 also has a middle 34 halfway between each of the ends 32. Each leg 30 has a thickness 36 which is measured in a direction substantially perpendicular to a direction that the leg 30 extends between the ends 32.

In one form of this invention the struts 20 are formed from legs 30 which have a uniform thickness 36 (FIG. 3). In a preferred form of this invention, however, the struts 20 feature legs 30' (FIG. 6) which have a thickness 36' which is variable. Specifically, the middle 34' of the legs 30' has a lesser thickness 36' than do the ends 32' of the legs 30'. When the struts 20 are radially expanded (along Arrow R of FIGS. 1, 4 and 5) little stress is experienced by the legs 30 of the struts 20 at the middle 34. In contrast, the ends 32 have a greater amount of stress because of the location of the adjacent free bends 40 and attachment bends 50. By enhancing the thickness 36' of the legs 30' so that the ends 32' have a greater thickness 36' than the middle 34' of the legs 30', the legs 30' are less susceptible to fracture resulting from the stress concentrations near the ends 32'.

Each leg 30 preferably has a similar length to other legs 30 throughout the strut 20 and throughout the stent 10. The greater the length of the legs 30, the greater the amount of radial expansion possible by the stent 10. However, if the legs 30 are too long than they will cause struts 20 to abut adjacent struts 20 when radially collapsed (as shown in FIGS. 1 and 7) and prevent complete radial contraction of the stent 10. Hence, the legs 30 preferably have a length substantially equal to one-half of the distance between adjacent struts 20 (measured trough to trough) to prevent abutting of the legs 30 of adjacent struts 20.

The free bends 40 are distinct from the attachment bends 50 in that the free bends 40 join two adjacent legs 30 together only, without any axial segments adjacent thereto connecting to adjacent struts 20. The attachment bends 50, in contrast, join two adjacent legs 30 together and also attach to either a tie bar 70, an angled link 80 or a straight link 90 (FIG. 10) which spans an adjacent gap 60 and attaches to an adjacent strut 20. The free bends 40 include an inner radius 42 on an inside of the bend 40 and defining a trough and an outer radius 44 on an outside of the bend 40 and defining a crest.

The width 46 of the free bend 40 is defined as a distance between the inner radius 42 and the outer radius 44. The inner radius 42 and outer radius 44 are rounded sufficiently to minimize stress concentrations adjacent the free bends 40 so that the free bends 40 do not provide a preferred location for fracture of the struts 20 of the stent 10. Additionally, an as shown in FIG. 6, some free bends 40' can be provided with an enhanced width 46, especially when such free bends 40' are joining adjacent legs 30' having ends 32' of enhanced thickness 36'. With the width 46 provided with an enhanced size, the ability of the free bends 40' of the strut 20 to resist fracture is enhanced. Alternatively, the free bends 40 can be provided with a width 46 substantially matching the thickness 36 of the legs 30.

The attachment bends 50 include a trough side 42 on an inside of each attachment bend 50 and a crest side 54 on an outer side of each attachment bend 50. A width 56 is defined as a distance between the trough side 52 and the crest side 54. As with the free bends 40, the attachment bends 50 can be provided with an enhanced width 56 which is greater than the width 46 of the legs 30 to enhance a strength of the struts 20 at the attachment bends 50. Alternatively, the attachment bends 50 can have a width 56 which matches a thickness 36 of the legs 30 (as shown in FIGS. 2).

In FIG. 6, some of the struts 20 (at a right side of FIG. 6) exhibit attachment bends 50' which do not exhibit an enhanced width 56 but rather which narrow to a width less than the thickness 36 of the legs 30 adjacent to the attachment bend 50'. Hence, a width 56 between a trough side 52' and a crest side 54' is reduced. Such an arrangement for the attachment bend 50' provides another alternative arrangement for configuration of the attachment bends 50 within the struts 20.

As shown in FIG. 7, the struts 20 can be radially collapsed to an extent where the legs 30 of the struts 20 are substantially parallel to each other and oriented axially, along arrow A. If the legs 30 are provided with enhanced thickness 36' adjacent the ends 32' (as shown in FIG. 6), clearance exists for such enhanced thickness 36' within the leg 30 pattern displayed in FIG. 7. This is partially because such thickness 36' enhancement adjacent the end 32' only occurs on a side of the legs 30' which transition into the outer radius 44 or crest side 54 and not the inner radius 42 or trough side 52. Hence, enhancing a thickness of the legs 30, at least a limited amount, does not restrict an ability of the struts 20 to radially collapse along with radial collapse of the stent 10.

Preferably, the stent 10 is chilled below a transition temperature such that the stent 10 is in a martensite phase when radially collapsed as shown in FIG. 7. An austenite phase for the stent 10 can either be provided as shown in FIG. 8 by reference numeral 10' or with a greater amount of radial expansion as shown in FIG. 9 by reference numeral 10". Even though the stent 10 shown in FIG. 7 is radially collapsed and in a martensite phase, it has a shape memory corresponding to the stent 10' of FIG. 8 or the stent 10" of FIG. 9, depending on the configuration and shape memory provided to the stent 10.

Radial expansion of the stent 10 by a factor of over four times can be achieved in certain circumstances. For instance, stents with a circumference of 0.1256 inches can be radial expanded to have a circumferential length of 0.6189 inches and stents having a circumferential length of 0.1995 inches can be radially expanded to up to 0.8645 inches in circumferential length.

With continuing reference to FIGS. 3 and 6–10, details of the gaps 60 and axial segments such as tie bars 70, angled links 80 and straight links 90 are described. Preferably, each strut 20 is spaced from adjacent struts 20 by a gap 60. Each gap 60 does not have a constant width but rather has a width which oscillates between minimums 62 and maximums 64. Each minimum 62 is defined as an axial distance between aligned crest sides 54 of attachment bends 50 or aligned outer radii 44 of free bends 40 of adjacent struts 20. Each maximum 64 is defined as an axial distance between axially aligned trough sides 52 of attachment bends 50 or inner radii 42 of free bends 40 of adjacent struts 20. Each gap 60 either has axial segments in the form of tie bars 70 attaching struts 20 adjacent the gap 60 together or has angled links 80 or straight links 90 spanning the gap 60 and joining adjacent struts 20 together. In gaps 60 which feature tie bars 70, the tie bars 70 join to attachment bends 50 of adjacent struts 20 at trough sides 52 of each attachment bend 50. Each tie bar 70 includes a first end 72 attached to the trough side 52 of one of the attachment bends 50 of one of the stents 20 and a second end 74 attached to a trough side 52 of an attachment bend 50 of the other strut 20.

Gaps 60 which feature angled links 80 or straight links 90 spanning said gaps 60 and attach to adjacent struts 20 at crest sides 54 of attachment bends 50 of adjacent struts 20. Each angled link 80 includes a first arm 82 and a second arm 84 attached together by an elbow 86. The first arm 82 attaches to the crest side 54 of the attachment bend 50 of one of the struts 20 and the second arm 84 of the angled link 80 attaches to the crest side 54 of the attachment bend 50 of the other strut 20 on the other side of the gap 60.

Similarly, the straight link 90 (FIG. 10) includes a first tip 92 attached to a crest side 54 of an attachment bend 50 of one of the struts 20 adjacent the gap 60 and a second tip 94 attached to the crest side 54 of the attachment bend 50 of the other strut 20 on an opposite side of the gap 60. The angled links 80 and straight links 90 essentially span the gap 60 at a minimum 62 in the gap 60. In contrast, the tie bars 70 span the gap 60 at maximums 64 of the gap 60. Hence, when the struts 20 are radially expanded and their amplitude 22 is reduced and their wavelength 24 is increased, an average width of gaps 60 spanned by the tie bars 70 is increased slightly and an average width of the gap 60 spanned by the angled links 80 or straight links 90 is decreased slightly. A net result is that an overall axial length of the stent 10 between a front end 12 and a rear end 14 (FIG. 3) remains constant regardless of the radial configuration of the stent 10. The angled links 80 are configured to allow the first arm 82 and second arm 84 to flex somewhat about the elbow 86 to provide a degree of flexibility to the stent 10. When the stent 10 is collapsed and being inserted into a body lumen (FIG. 7) angled links 80 are desirable to provide enhanced flexibility to the stent 10.

While FIGS. 1–10 show the angled links 80 and straight links 90 offset circumferentially with respect to locations of the tie bar 70, an acceptable alternative arrangement is to have the angled links 80 or straight links 90 axially aligned along a common line with the tie bars 70.

Figure 11:
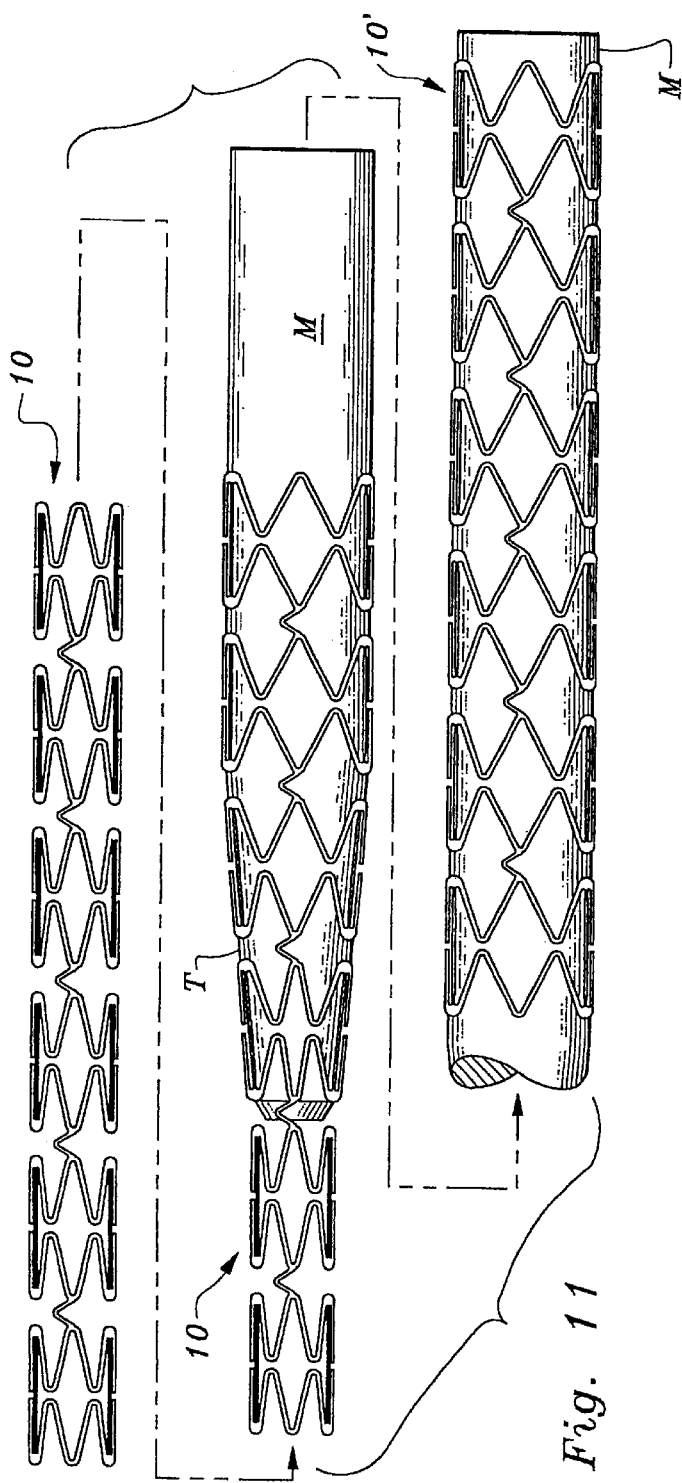
FIG. 11 is a top plan view of a series of steps involved in the process of forcing a stent, such as that which is shown in FIGS. 1–5, onto a mandrel for enhancing a radial diameter of the stent.
Figure 12:
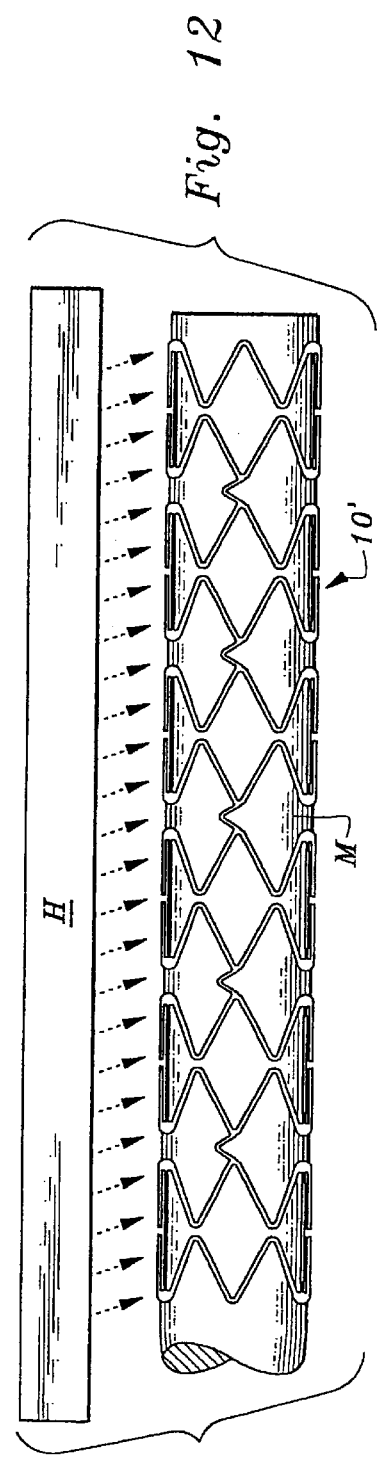
FIG. 12 is a top plan view of a heat applying step involved in altering a shape memory for the stent shown therein.

With particular reference to FIGS. 11 and 12, details of the formation of the stent 10 are disclosed. Initially, the stent 10 is in the form of a solid cylindrical tube of the appropriate shape memory material, such as a Nickel-Titanium alloy. Preferably, a diameter of this original tube of material is intermediate between a desired collapsed configuration diameter and a desired expanded configuration diameter. The tube is then processed, such as by laser cutting, to remove material where it is not needed such that the tube is reduced to the stent 10 having the series of wave-like struts 20 circumferentially surrounding the cylindrical contour of the stent 10 and a series of axial segments such as tie bars 70, angled links 80 or straight links 90 (FIGS. 1-10) joining the adjacent struts 20 together.

The stent 10 is preferably then treated to modify its shape memory. Specifically, the stent 10 is placed onto a mandrel M (FIG. 11) by moving the stent 10 axially over a taper T on the mandrel M with sufficient force that the stent 10' in radially expanded configuration is entirely upon the mandrel M. The mandrel M is provided with a diameter which matches a desired diameter for the radially expanded configuration of the stent 10'. Once upon the mandrel M, the stent 10' still has a shape memory corresponding to its diameter before it was placed upon the mandrel M. If the stent 10 were removed from the mandrel M, this shape memory would cause the stent 10 to return to its original diameter. To enhance the ease with which the stent 10 is placed upon the mandrel M, the stent 10 can be cooled to below a transition temperature so that the stent 10 is in a martensite phase with a lower yield strength.

To alter the shape memory of the stent 10', the stent 10' with mandrel M preferably still adjacent the stent 10' is subjected to heat treatment from a heat source H until the stent 10' has its temperature elevated up to at least 300° C. Preferably, the stent 10' has its temperature elevated up to a range of between 500° C. and 800° C. The stent 10' is beneficially held at this elevated temperature for an amount of time necessary for the stent 10' to have its shape memory "erased" and to take on a new shape memory corresponding to the diameter of the mandrel M. The stent 10' can then be cooled and removed from the mandrel M. Once removed from the mandrel M, the stent 10' now has its shape memory corresponding to the diameter of the mandrel M and hence will not contract back to its original shape. The shape memory for the stent 10' is now configured as desired.

Figure 13:
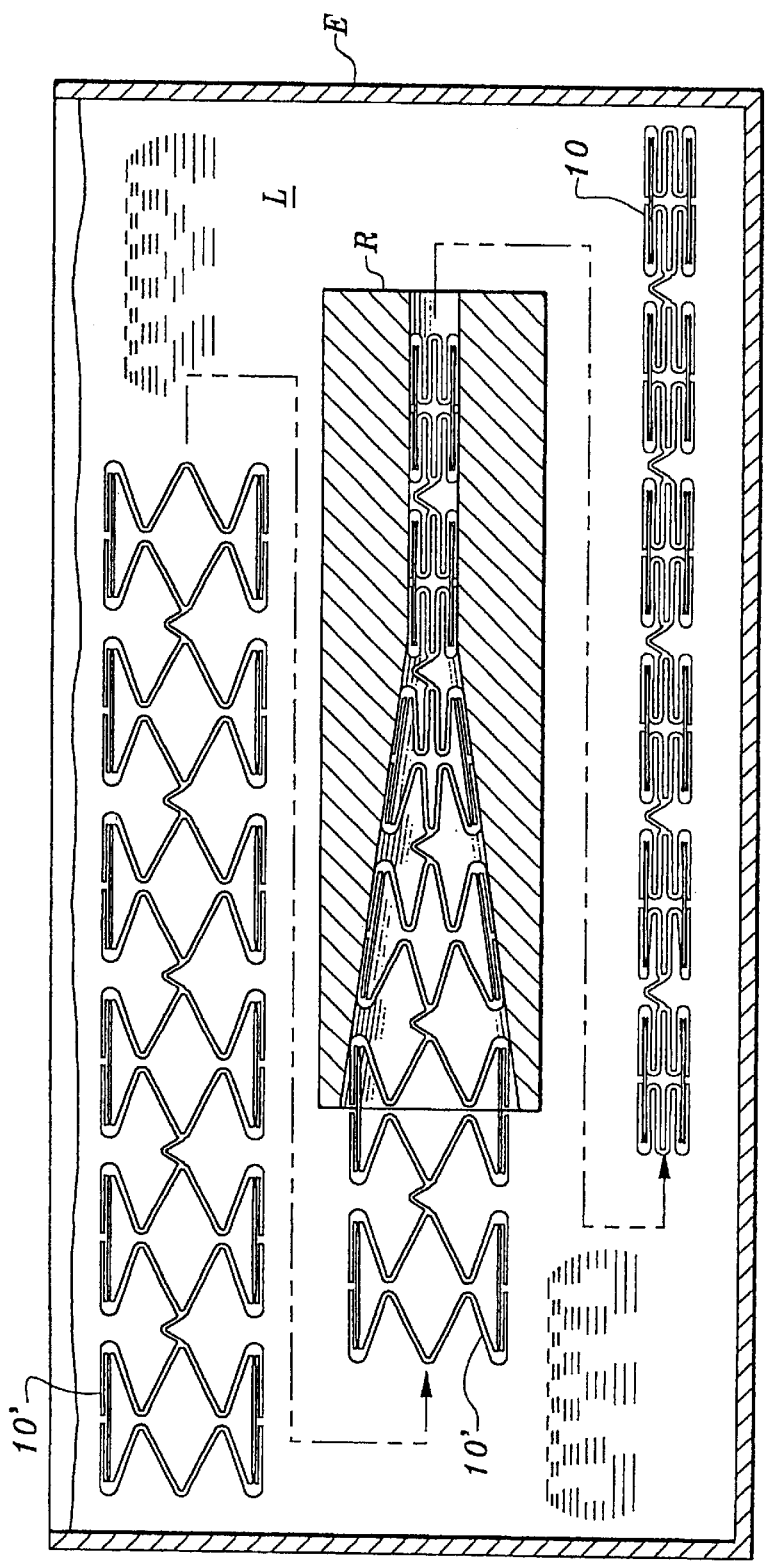
FIG. 13 is a front elevation view of a series of steps involved in radially collapsing the stent from the radially expanded configuration to the radially collapsed configuration while the stent is cooled below a transformation temperature and in a martensite phase.

With respect to FIGS. 13–17, details in the steps involved in radially collapsing the stent 10' down to a collapsed stent 10 for implantation within a body lumen is described. Initially, the stent 10' is cooled such as by placing the stent 10' within a liquid coolant L (FIG. 13). The stent 10' transitions into a martensite phase where it can be easily manipulated such as by radially collapsing the stent 10' by forcing the stent 10' through a reduction die R while at the reduced temperature and in the martensite phase. The liquid L within the enclosure E must have a temperature below a transition temperature which causes the stent 10 to change from its austenite phase to its martensite phase. Once the stent 10 has been radially collapsed to its reduced diameter configuration (see also FIG. 7) the stent 10 now has a diameter which facilitates more convenient location within a body lumen. The stent 10 maintains its shape memory corresponding to the diameter of the mandrel M when the stent 10' was radially expanded onto the mandrel M and experienced its heat treatment.

Figure 14:
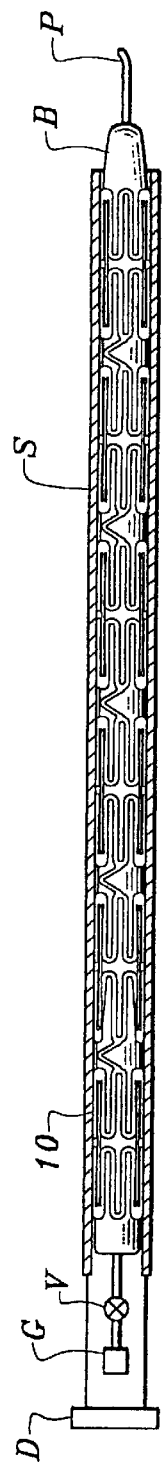
FIG. 14 is a top plan view of the stent of FIGS. 1–5 within a surgical implantation apparatus with portions of the apparatus cut away to reveal interior details thereof.

The stent 10 is then placed upon a balloon catheter B with a catheter probe P extending from one end thereof and with a sleeve S overlying the stent 10 (FIG. 14). Preferably, the balloon catheter B is coupled to a compressed gas source G through a valve B and the sleeve S is attached to a sleeve retraction device D. Preferably, the stent 10 remains at a temperature below its transition temperature and in a martensite phase for as long as possible before implantation into the body lumen. The assembly of stent 10, balloon catheter B and sleeve S are then passed together through the desired body lumen pathways until the assembly is located at the position where implantation of the stent 10 is desired.

The sleeve retraction device D is utilized to remove the sleeve S from the stent 10 (FIG. 15). Once the sleeve S has been removed, gas from the compressed gas source G is passed through the valve V and into the balloon catheter B, causing the balloon catheter B to expand and causing the stent 10 to radially expand into the radially expanded stent 10'. The stent 10' will then be in physical contact with an inner surface I of the lumen wall W. The shape memory of the stent 10' may cause the stent 10' to expand radially without requiring inflation of the balloon catheter B. However, expansion of the balloon catheter B assists the stent 10' in effectively converting to its shape memory diameter adjacent the lumen wall W. The balloon catheter B can then be removed and the stent 10' remains within the lumen adjacent the inner surface I of the lumen wall W.

Because the stent 10 has its transition temperature below normal body temperature, the stent 10 will be in its austenite phase and have enhanced yield strength. Hence, radial forces such as blows to the patient adjacent where the stent 10' has been implanted can be resiliently received by the stent 10' without permanent deformation of the stent 10'. A stronger and more elastic support results with the shape memory Nickel-Titanium stent 10' than is provided by stents of other non-shape memory materials.

Moreover, having thus described the invention is should be apparent that various modifications to this invention could be resorted to without departing from the scope of this invention. This detailed description of the preferred embodiments of this invention is provided to enable one skilled in the art to practice this invention and to disclose a best mode for practicing this invention but is not intended to limit in any way the scope of the claims to this invention.

What is claimed is:

1. A radially expandable non-axially contracting surgical stent comprising:
    a generally cylindrical contour;
    a plurality of circumferential segments and axially extending segments of a shape memory nickel-titanium alloy;
    at least two of said circumferential segments each extending in a substantially circumferential direction around said cylindrical contour of said stent;
    said at least two circumferential segments each including a series of wave-like bends therein, each said bend including a trough and a crest, said trough defining a portion of said bend where said bend is more distant from an adjacent circumferential segment than other portions of said bend, said crest defining a portion of said bend where said bend is closer to an adjacent circumferential segment than other portions of said bend;
    said at least two circumferential segments oriented adjacent each other with a first gap located between said at least two circumferential segments;
    said first gap having at least one axially extending segment spanning said first gap and linking said at least two circumferential segments together, said axially extending segment linking said at least two circumferential segments at locations on said at least two circumferential segments in which troughs thereof are longitudinally aligned; and
    wherein said at least one axially extending segment and said trough locations linked by said at least one axially extending segment are substantially coplanar after said stent is expanded radially.

2. The sent of claim 1 wherein said axially extending segment spanning said first gap maintains its length.

3. The stent of claim 1 wherein said axially extending segment spans said first gap and links to said circumferential segments substantially at troughs in said circumferential segments.

4. The stent of claim 3 wherein each said circumferential segment is spaced from adjacent circumferential segments by gaps such that a number of gaps equals a number of circumferential segments minus one, said gaps including odd numbered gaps and even numbered gaps with each said odd numbered gap having at least one axially extending segment attached to adjacent said circumferential segments at troughs in said circumferential segments and each said even numbered gap having at least one axially extending segment attached to adjacent said circumferential segments at said crests in circumferential segments.

5. The stent of claim 1 wherein said circumferential segments include a plurality of substantially linear legs extending between each bend in said circumferential segments.

6. The stent of claim 5 wherein said legs have a length which is substantially equal to one-half of a distance axially between troughs in adjacent ones of said circumferential segments.

7. The stent of claim 1 wherein said at least three of said circumferential segments extend in a substantially circumferential direction around said cylindrical contour of said stent and define a gap between each pair of adjacent circumferential segments, each said gap having at least one axially extending segment spanning said gap and linking the adjacent circumferential segments together, and further wherein said axially extending segment spanning said first gap is circumferentially offset with respect to axially extending segments in adjacent of said gaps.

8. The stent of claim 1 wherein at least three of said circumferential segments extend in a substantially circumferential direction around said cylindrical contour of said stent and define a gap between each pair of adjacent circumferential segments, each said gap having at least one axially extending segment spanning said gap and linking the adjacent circumferential segments together, and further wherein said axially extending segment spanning said first gap is axially aligned with an axially extending segment spanning adjacent of said gaps.

9. The stent of claim 1 wherein at least three of said circumferential segments extend in a substantially circumferential direction around said cylindrical contour of said stent and define a gap between each pair of adjacent circumferential segments, each said gap having at least one axially extending segment spanning said gap linking the adjacent circumferential segments together, and further wherein said axially extending segment spanning at least one gap other than said first gap links to said circumferential segments at crests in said circumferential segments.

10. The stent of claim 9 wherein each said circumferential segments is spaced from adjacent circumferential segments by gaps such that a number of gaps equals a number of circumferential segments minus one, said gaps including odd numbered gaps and even numbered gaps with each said odd numbered gap having at least one axially extending segment attached to adjacent said circumferential segments at troughs in said circumferential segments and each said even numbered gap having at least one axially extending segment attached to adjacent said circumferential segments at crests in said circumferential segments.

\* \* \* \* \*